US012738402B2

(12) United States Patent
Wang et al.

(10) Patent No.: US 12,738,402 B2
(45) Date of Patent: Sep. 15, 2026

(54) MAGNETIC BALL CALIBRATION METHOD AND MAGNETIC BALL CALIBRATION APPARATUS

(71) Applicant: Ankon Medical Technologies ( Shanghai) Co., LTD, Shanghai (CN)

(72) Inventors: Qingqing Wang, Shanghai (CN); Junjie Wang, Shanghai (CN); Xiaodong Duan, Plano, TX (US)

(73) Assignees: Ankon Medical Technologies (Shanghai) Co., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 227 days.

(21) Appl. No.: 18/833,931

(22) PCT Filed: Jan. 16, 2023

(86) PCT No.: PCT/CN2023/072316
§ 371 (c)(1),
(2) Date: Jul. 29, 2024

(87) PCT Pub. No.: WO2023/143170
PCT Pub. Date: Aug. 3, 2023

(65) Prior Publication Data

US 2025/0157710 A1 May 15, 2025

(30) Foreign Application Priority Data

Jan. 28, 2022 (CN) ......................... 202210104917.0

(51) Int. Cl.
*H01F 7/02* (2006.01)
*A61B 1/00* (2006.01)
(Continued)

(52) U.S. Cl.
CPC ........ *H01F 7/0294* (2013.01); *A61B 1/00057* (2013.01); *A61B 1/00158* (2013.01); *A61B 1/041* (2013.01); *A61B 5/062* (2013.01)

(58) Field of Classification Search
CPC ............... H01F 7/0294; A61B 1/00057; A61B 1/00158; A61B 1/041; A61B 5/062; A61B 5/073; A61B 1/00006; G01R 35/00
See application file for complete search history.

(56) References Cited

U.S. PATENT DOCUMENTS

2005/0160609 A1 7/2005 Kwon et al.
2018/0321036 A1 11/2018 Kobayashi et al.

FOREIGN PATENT DOCUMENTS

CN 1956675 A 5/2007
CN 106569150 A 4/2017
(Continued)

*Primary Examiner* — Mohamad A Musleh
(74) *Attorney, Agent, or Firm* — Treasure IP Group, LLC

(57) ABSTRACT

A magnetic ball calibration method and a magnetic ball calibration apparatus is disclosed. The method includes: rotating a magnetic ball around a first axis and a second axis, and acquiring detection data of three-axis magnetic field components at a detection position during rotation; obtaining a calibration position of the magnetic ball according to the detection data; and calibrating the magnetic ball according to the calibration position. When the magnetic ball is located at the calibration position, the magnetic polarization direction of the magnetic ball coincides with the second axis; the first axis is perpendicular to the second axis; the three-axis magnetic field components include an X-axis magnetic field component, a Y-axis magnetic field component and a Z-axis magnetic field component; the direction of the Z-axis magnetic field component and the Y-axis magnetic field component coincide with the direction of the second axis and the first axis, respectively.

11 Claims, 9 Drawing Sheets

(51) Int. Cl.
*A61B 1/04* (2006.01)
*A61B 5/06* (2006.01)

(56) References Cited

FOREIGN PATENT DOCUMENTS

| | | | | |
|---|---|---|---|---|
| CN | 107405052 A | | 11/2017 |
| CN | 109620104 A | | 4/2019 |
| CN | 110360925 A | | 10/2019 |
| CN | 210095673 U | * | 2/2020 |
| CN | 111289923 A | | 6/2020 |
| CN | 113729599 A | | 12/2021 |

* cited by examiner

MAGNETIC BALL CALIBRATION METHOD AND MAGNETIC BALL CALIBRATION APPARATUS

CROSS-REFERENCE OF RELATED APPLICATIONS

The application is a National Phase Application of PCT International Application No. PCT/CN2023/072316, International Filing Date Jan. 16, 2023, published Aug. 3, 2023 as International Publication Number WO2023/143170A1, which claims priority from Chinese Patent Application No. 202210104917.0, filed Jan. 28, 2022, all of which are incorporated herein by reference in their entirety.

FIELD OF INVENTION

The present invention relates to a magnetic control technique and a capsule endoscope technique, and more particularly to a magnetic ball calibration method and a magnetic ball calibration apparatus.

BACKGROUND

Capsule endoscopes, which can be actively controlled by external magnetic control devices, provide detailed and comprehensive examinations. Compared to traditional endoscopes, capsule endoscopes offer better comfort and lower risk of cross-infection, leading to the increased adoption in clinical applications.

For a magnetically controlled capsule endoscope system, a permanent magnet (usually a magnetic sphere, i.e., magnetic ball) on the external magnetic control device is the core component for controlling the movement of the capsule endoscope. By controlling the orientation and/or position of the magnetic ball, the magnetic field changes, enabling the capsule endoscope to achieve corresponding movements such as translation, rotation, and flip according to the changing magnetic field. The magnetic ball influences the orientation of the capsule endoscope through the direction of the magnetic field. In actual use, uncertainties in the direction of the magnetic field or deviations in the position of the magnetic poles of the permanent magnet can cause significant errors in the orientation angle of the capsule endoscope, affecting the accuracy of the orientation of the capsule endoscope and, consequently, the accuracy of its information collection. For the external magnetic control device of the capsule endoscope, it is necessary to calibrate the direction of the magnetic ball during use.

In current technology, multiple sensors are typically used to obtain magnetic field data to determine the direction of the magnetic field of the magnetic ball. Although this method can accurately determine the direction of the magnetic ball, the process is cumbersome and complex, making it unsuitable for widespread application.

Therefore, there is a need for a simpler, more convenient, and accurate magnetic ball calibration method and magnetic ball calibration apparatus.

SUMMARY OF THE INVENTION

In view of the above problems, it is an object of the present invention to provide a magnetic ball calibration method and a magnetic ball calibration apparatus, thus allowing for accurate, convenient, and quick calibration of the magnetic ball.

According to one aspect of present invention, a magnetic ball calibration method is provided, comprising the following steps:

rotating a magnetic ball around a first axis and a second axis, and acquiring detection data of three-axis magnetic field components at a detection position during rotation;

obtaining a calibration position of the magnetic ball according to the detection data; and calibrating the magnetic ball according to the calibration position of the magnetic ball;

where when the magnetic ball is located at the calibration position, the magnetic polarization direction of the magnetic ball coincides with the second axis;

the first axis is perpendicular to the second axis;

the three-axis magnetic field components comprise an X-axis magnetic field component, a Y-axis magnetic field component and a Z-axis magnetic field component;

the direction of the Z-axis magnetic field component coincides with the direction of the second axis, and the direction of the Y-axis magnetic field component coincides with the direction of the first axis.

Optionally, the method comprises rotating the magnetic ball around the first axis by a first angle, and acquiring detection data of the three-axis magnetic field components at a detection position during the rotation;

obtaining a first calibration position $V_0$ of the magnetic ball rotating around the first axis according to the detection data of the three-axis magnetic field components and the corresponding rotation angle during the rotation of the magnetic ball around the first axis by the first angle;

rotating the magnetic ball to the first calibration position $V_0$, and then rotating the magnetic ball around the first axis by a second angle;

rotating the magnetic ball around the second axis by a third angle, and acquiring detection data of the three-axis magnetic field components at a detection position during the rotation;

obtaining a second calibration position $H_0$ of the magnetic ball rotating around the second axis according to the detection data of the three-axis magnetic field components and the corresponding rotation angle during the rotation of the magnetic ball around the second axis by the third angle.

Optionally, the first angle is greater than 360°, or is 540°;

the second angle is greater than or equal to 10° and smaller than or equal to 80°, or is 45°;

the third angle is greater than 360°, or is 540°.

Optionally, obtaining the first calibration position V0 of the magnetic ball rotating around the first axis comprises:

determining the position of the magnetic ball corresponding to the maximum value or minimum value of a magnetic field strength in the Z-axis direction as the first calibration position $V_0$ according to the detection data of the three-axis magnetic field components and the corresponding rotation angle during the rotation of the magnetic ball around the first axis by the first angle;

obtaining the second calibration position $H_0$ of the magnetic ball rotating around the second axis comprises:

determining the rotation angle corresponding to the maximum value or minimum value of the magnetic field strength in the Y-axis direction as the second calibration position $H_0$ according to the detection data of the three-axis magnetic field components and the corresponding rotation angle during the rotation of the magnetic ball around the second axis by the third angle;

or, determining the rotation angle corresponding to the maximum value or minimum value of the magnetic field strength in the X-axis direction as the second calibration position $H_0$ according to the detection data of the three-axis magnetic field components and the corresponding rotation angle during the rotation of the magnetic ball around the second axis by the third angle.

Optionally, obtaining the first calibration position $V_0$ of the magnetic ball rotating around the first axis comprises:

obtaining a curve of the magnetic field strength in the Z-axis direction with respect to the rotation angle of the magnetic ball according to the detection data during the rotation of the magnetic ball around the first axis by the first angle, where the rotation angle of the magnetic ball corresponding to the maximum value or minimum value on the curve is the first calibration position V0; and obtaining the second calibration position $H_0$ of the magnetic ball rotating around the second axis comprises:

obtaining a curve of the magnetic field strength in the Y-axis direction with respect to the rotation angle of the magnetic ball according to the detection data during the rotation of the magnetic ball around the second axis by the third angle, and determining the rotation angle corresponding to the maximum value or minimum value of the magnetic field strength in the Y-axis direction as the second calibration position $H_0$;

or, determining the rotation angle corresponding to the maximum value or minimum value of the magnetic field strength in the X-axis direction as the second calibration position H0 according to the detection data of the three-axis magnetic field components and the corresponding rotation angle during the rotation of the magnetic ball around the second axis by the third angle.

According to another aspect of the present invention, a magnetic ball calibration apparatus is provided, where the magnetic ball comprises magnetic poles along a main axis direction, comprising:

a driving unit for driving the magnetic ball to rotate, comprising a first driving unit and a second driving unit, where the first driving unit is used to drive the magnetic ball to rotate around the first axis, and the second driving unit is used to drive the magnetic ball to rotate around the second axis, and calibrate the magnetic ball based on the calibration position;

a three-axis magnetic field sensor, disposed adjacent to the magnetic ball to obtain detection data of three-axis magnetic field components during rotation of the magnetic ball; and a data processing unit, connected to the three-axis magnetic field sensor to receive the detection data of the three-axis magnetic field components, and obtain the calibration position of the magnetic ball according to the detection data changing with the rotation angle during rotation of the magnetic ball, where, when the magnetic ball is at the calibration position, the main axis coincides with the second axis;

the first axis is perpendicular to the second axis;

the three-axis magnetic field components comprise an X-axis magnetic field component, a Y-axis magnetic field component and a Z-axis magnetic field component;

the direction of the Z-axis magnetic field component coincides with the direction of the second axis, and the direction of the Y-axis magnetic field component coincides with the direction of the first axis.

Optionally, the first driving unit is used to drive the magnetic ball to rotate around the first axis by a first angle;

the data processing unit comprises a third processing unit, the third processing unit used for obtaining a first calibration position $V_0$ of the magnetic ball rotating around the first axis according to the detection data of the three-axis magnetic field components and the corresponding rotation angle during the rotation of the magnetic ball by the first angle around the first axis;

the first driving unit rotates the magnetic ball to the first calibration position $V_0$, and the first driving unit is also used to rotate the magnetic ball around the first axis by a second angle;

the second driving unit is used to drive the magnetic ball to rotate around the second axis by a third angle;

the data processing unit comprises a fourth processing unit, the fourth processing unit used for obtaining a second calibration position $H_0$ of the magnetic ball rotating around the second axis according to the detection data of the three-axis magnetic field components and the corresponding rotation angle during the rotation of the magnetic ball by the third angle around the second axis.

Optionally, the first angle is greater than 360°, or is 540°;

the second angle is greater than or equal to 10° and smaller than or equal to 80°, or is 45°;

the third angle is greater than 360°, or is 540°.

Optionally, the third processing unit is also used for:

determining the position of the magnetic ball corresponding to the maximum value or minimum value of a magnetic field strength in the Z-axis direction as the first calibration position $V_0$ according to the detection data of the three-axis magnetic field components and the corresponding rotation angle during the rotation of the magnetic ball around the first axis by the first angle;

the fourth processing unit is also used for:

determining the rotation angle corresponding to the maximum value or minimum value of the magnetic field strength in the Y-axis direction as the second calibration position $H_0$ according to the detection data of the three-axis magnetic field components and the corresponding rotation angle during the rotation of the magnetic ball around the second axis by the third angle;

or, determining the rotation angle corresponding to the maximum value or minimum value of the magnetic field strength in the X-axis direction as the second calibration position $H_0$ according to the detection data of the three-axis magnetic field components and the corresponding rotation angle during the rotation of the magnetic ball around the second axis by the third angle.

Optionally, the third processing unit is also used for:

obtaining a curve of the three-axis magnetic field component in the Z-axis direction with respect to the rotation angle of the magnetic ball according to the detection data during the rotation of the magnetic ball around the first axis by the first angle, where the rotation angle of the magnetic ball corresponding to the maximum value or minimum value on the curve is the first calibration position $V_0$;

the fourth processing unit is also used for:

obtaining a curve of the three-axis magnetic field component in the Y-axis direction with respect to the rotation angle of the magnetic ball according to the detection data during the rotation of the magnetic ball around the second axis by the third angle, and determining the rotation angle corresponding to the maximum value or minimum value of the magnetic field strength in the Y-axis direction as the second calibration position $H_0$;

or, determining the rotation angle corresponding to the maximum value or minimum value of the magnetic field strength in the X-axis direction as the second calibration position $H_0$ according to the detection data of the three-axis magnetic field components and the corresponding rotation angle during the rotation of the magnetic ball by the third angle.

Optionally, the first axis or the second axis passes through the three-axis magnetic field sensor; and the detection position comprises the position where the three-axis magnetic field sensor is located.

According to the embodiments of the present invention, in the magnetic ball calibration apparatus and magnetic ball calibration method, a three-axis magnetic field sensor is used to determine the direction of the magnetic ball, so that the operation is simple, allowing for convenient, quick, and accurate calibration of the magnetic ball, providing a precise basis for determining the orientation of the capsule endoscope.

According to the magnetic ball calibration apparatus of the embodiments of the present invention, the three-axis magnetic field sensor and the two rotation axes are fixed, facilitating the integrated design of the magnetic ball calibration apparatus.

According to the magnetic ball calibration apparatus and magnetic ball calibration method of the embodiments of the present invention, different angles of rotation of the magnetic ball are sequentially used to complete the calibration, achieving high accuracy in calibration, which is conducive to accurately controlling the posture of the capsule endoscope.

BRIEF DESCRIPTION OF THE DRAWINGS

The above and other objects, features and advantages of the present invention will be apparent upon consideration of the following detailed description, taken in conjunction with the accompanying drawings, in which the reference characters refer to like parts throughout and in which.

DETAILED DESCRIPTION

Figure 1:
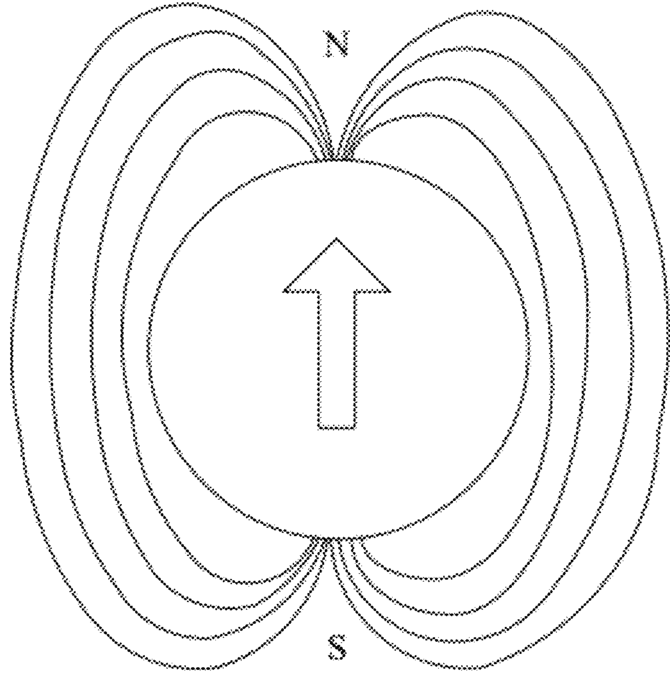
FIG. 1 shows a schematic diagram of a magnetic field distribution of a magnetic ball according to an embodiment of the present invention.

Various embodiments of which the present invention will be described in more detail below with reference to the accompanying drawings. In the drawings, the same elements are represented by the same or similar markings. For simplicity and clarity of illustration, elements shown in the drawings are not drawn to scale. In addition, some well-known elements may not be shown in the drawings.

Specific embodiments of the present invention are described in further details below in conjunction with the accompanying drawings and embodiments. Many specific details of the present invention are described below, such as the structure, materials, dimensions, processing and techniques of components, in order to understand the present invention more clearly. However, as may be understood by those skilled in the art, the present invention may be implemented without following these particular details.

It should be understood that, when a layer or an area is referred to as being "above" or "over" another layer or another area in describing the structure of a component, it may refer to being directly on another layer or another area, or containing other layers or areas between it and another layer or another area. Also, if the component is turned over, the layer or area can be "under" or "below" another layer or another area.

FIG. 1 shows a schematic diagram of a magnetic field distribution of a magnetic ball according to an embodiment of the present invention. As shown in FIG. 1, in an embodiment of the present invention, the magnetic ball 10 comprises magnetic poles along the main axis direction (specific direction of the magnetic field). The main axis coincides with the line connecting the N pole and S pole of the magnetic ball, which is a specific axis of the magnetic ball. According to an embodiment of the present invention, the two ends of a certain diameter of the magnetic ball 10 are the N pole and S pole, respectively. The magnetic field distribution of the magnetic ball 10 is shown, for example, by the magnetic induction lines as in FIG. 1.

Figure 2:
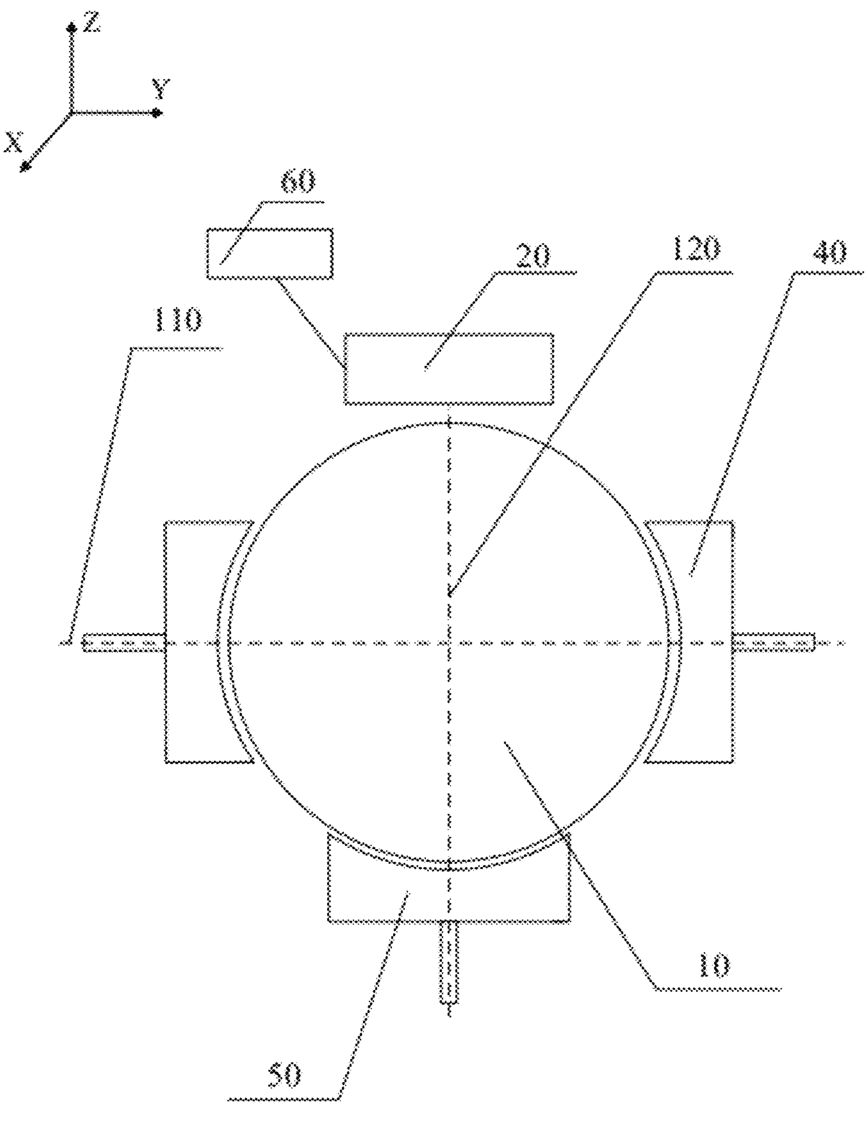
FIG. 2 shows a perspective schematic diagram of a magnetic ball calibration apparatus according to a first embodiment of the present invention.

FIG. 2 shows a perspective schematic diagram of a magnetic ball calibration apparatus according to a first embodiment of the present invention. As shown in FIG. 2, in one aspect, the embodiment of the present invention provides a magnetic ball calibration apparatus, comprising a three-axis magnetic field sensor 20, a driving unit, and a data processing unit 60. The magnetic ball 10 comprises a first direction and a second direction, where the first direction is the direction in which the magnetic ball 10 rotates around a first axis 110, and the second direction is the direction in which the magnetic ball 10 rotates around a second axis 120.

The driving unit comprises a first driving unit 40 and a second driving unit 50;

the first driving unit 40 is used to drive the magnetic ball 10 to rotate in the first direction.

the second driving unit 50 is used to drive the magnetic ball 10 to rotate in the second direction;

the three-axis magnetic field sensor 20 is disposed adjacent to the magnetic ball 10 to obtain detection data of the three-axis magnetic field components during rotation of the magnetic ball 10; and the data processing unit 60 is connected to the three-axis magnetic field sensor 20 to receive the detection data of the three-axis magnetic field components, and obtain the calibration position of the magnetic ball 10 according to the detection data changing with the rotation angle during the rotation of the magnetic ball.

When the magnetic ball 10 is in the calibration position, the main axis coincides with the direction of the second axis. The first axis and the second axis are perpendicular to each other. The three-axis magnetic field components comprise an X-axis magnetic field component, a Y-axis magnetic field component, and a Z-axis magnetic field component. The direction of the Z-axis magnetic field component coincides with the direction of the second axis. The direction of the Y-axis magnetic field component coincides with the direction of the first axis.

Specifically, the magnetic ball 10 can rotate around the first axis 110 and/or the second axis 120 (i.e., rotate in the first direction and/or the second direction). During the movement of the magnetic ball 10, the first axis 110 maintains a fixed orientation relative to the second axis 120 (for example, a fixed angle). Optionally, the position of the rotating shaft of the first axis 110 and/or the second axis 120 is fixed, or the rotating shaft is fixedly installed in a capsule endoscope system. Preferably, both the first axis 110 and the second axis 120 pass through the center of the magnetic ball 10, and the first axis 110 is perpendicular to the second axis 120. Accordingly, a three-axis (three-dimensional rectangular coordinate system) is established. Optionally, in this coordinate system, the line where the first axis 110 is located is the Y-axis, and the center of the magnetic ball 10 is the origin. The three-axis magnetic field components are the magnetic field components on the three axes of the three-dimensional rectangular coordinate system.

Optionally, the three-axis magnetic field components are determined by the direction of the three-axis magnetic field sensor 20 itself, specifically by the chip (not shown) of the sensor 20. The three-axis directions of the three-axis magnetic field components are: vertically upward from the plane of the chip as the $Z_1$ axis, $X_1$ axis, and $Y_1$ axis parallel to the plane of the chip. The directions of the $X_1$ axis, $Y_1$ axis, and $Z_1$ axis of the chip correspond to the directions of the X-axis, Y-axis, and Z-axis in the three-dimensional rectangular coordinate system. Later, the three-axis magnetic field components are described using the three axes of the three-dimensional rectangular coordinate system, i.e., the three-axis magnetic field components comprise an X-axis magnetic field component, a Y-axis magnetic field component, and a Z-axis magnetic field component. The direction of the Z-axis magnetic field component coincides with the direction of the second axis 120. The direction of the Y-axis magnetic field component coincides with the direction of the first axis 110.

Figure 3:
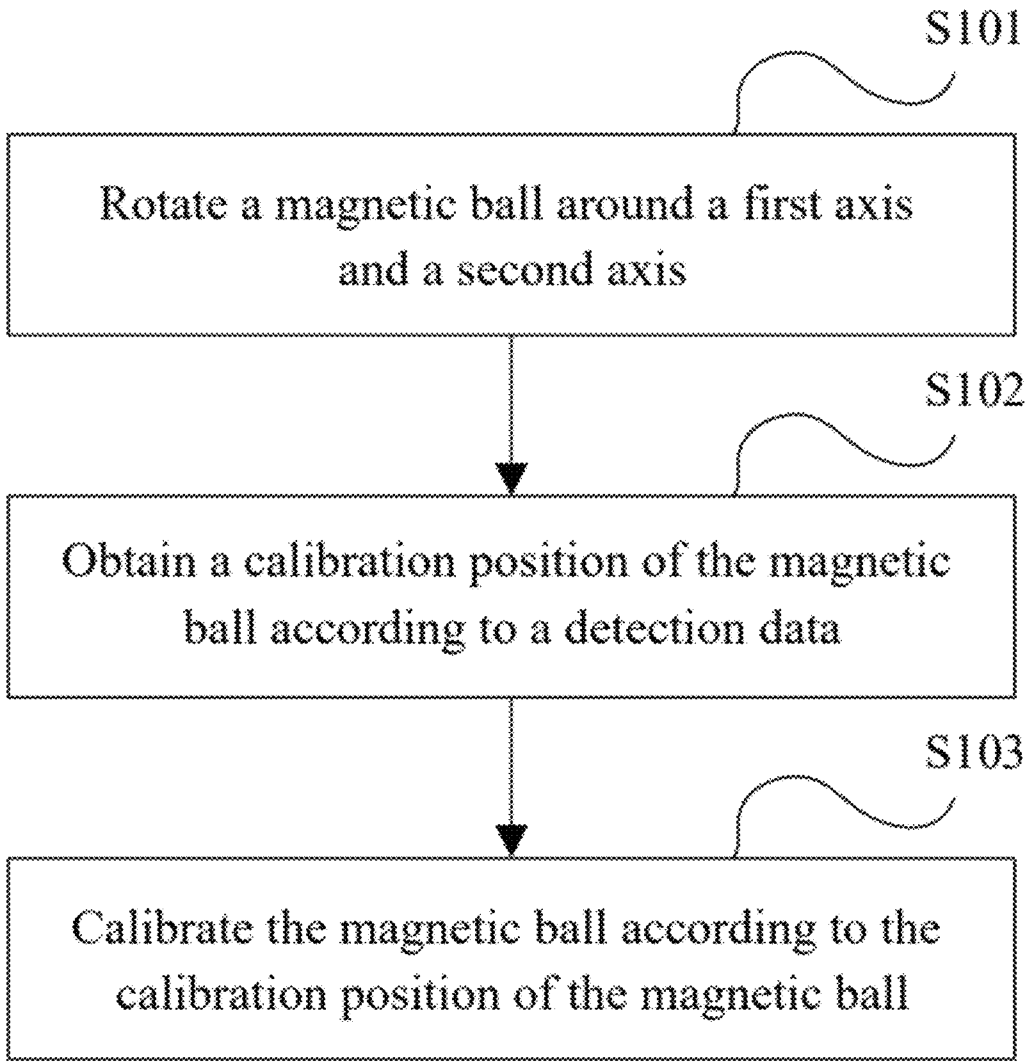
FIG. 3 shows a flowchart of a magnetic ball calibration method according to the first embodiment of the present invention.

Referring to FIG. 3, the magnetic ball calibration method according to the apparatus may comprise the following steps:

- the magnetic ball 10 rotating around the first axis 110 and the second axis 120, and the three-axis magnetic field sensor 20 acquiring detection data of the three-axis magnetic field components at a detection position during the rotation;
- obtaining a calibration position of the magnetic ball 10 according to the detection data; and
- calibrating the magnetic ball 10 according to the calibration position of the magnetic ball 10.

During calibration, the first driving unit 40 drives the magnetic ball 10 to rotate by a preset angle around the first axis 110 (in the first direction), and the second driving unit 50 drives the magnetic ball 10 to rotate by a predetermined angle around the second axis 120 (in the second direction). Optionally, the first driving unit 40 drives the magnetic ball 10 to rotate around the first axis 110 (by a first angle), and the second driving unit 50 drives the magnetic ball 10 to rotate around the second axis 120 (by a third angle). Additionally, the magnetic ball calibration apparatus also comprises a three-axis magnetic field sensor 20 placed adjacent to the magnetic ball 10 to detect the magnetic field strength of the magnetic ball 10, especially the magnetic field strength change during the rotation of the magnetic ball 10.

In one embodiment, the first driving unit 40 may be located on the side of the magnetic ball 10 (for example, on both sides of the magnetic ball 10) to drive the magnetic ball 10 to rotate around the first axis 110.

More specifically, the three-axis magnetic field sensor 20 is located directly above the magnetic ball 10 (as shown in FIG. 2, i.e., along the Z-axis at the top of the magnetic ball 10) to detect the magnetic field strength of the magnetic ball 10 in the three-axis direction (i.e., the magnetic field strength in each direction in three-dimensional space). In other embodiments of the present invention, the three-axis magnetic field sensor 20 may also be disposed in other positions as long as it can accurately obtain the magnetic field strength of the magnetic ball 10 during the rotation. In one specific embodiment, the detection data may comprise the three-axis magnetic field strength components and the rotation angle of the magnetic ball 10.

The three-axis magnetic field sensor 20 is disposed adjacent to the magnetic ball 10 to detect the detection data of the three-axis magnetic field components during the rotation of the magnetic ball 10 (for example, detecting the magnetic field strength of the magnetic ball 10 in each direction in three-dimensional space). In an embodiment of the present invention, the distance between the three-axis magnetic field sensor 20 and the surface of the magnetic ball 10 can be adjusted based on the magnetic field strength of the magnetic ball 10 and/or the sensitivity of the three-axis magnetic field sensor 20. The present invention does not further limit the distance between the three-axis magnetic field sensor 20 and the outer surface of the magnetic ball 10, as long as the three-axis magnetic field sensor 20 can accurately acquire the magnetic field strength of the magnetic ball 10. Further, in this embodiment, the first driving unit 40 may directly control the rotation of the magnetic ball 10, or may also control the rotation of the magnetic ball 10 through a transmission component (not shown in FIGs). This is not elaborated further here.

The data processing unit 60 is connected to the three-axis magnetic field sensor 20 to receive the detection data of the three-axis magnetic field components, and obtain the calibration position of the magnetic ball 10 according to the detection data changing with the rotation of the magnetic ball 10. The connection between the data processing unit 60 and the three-axis magnetic field sensor 20 can be either wired or wireless. In a specific embodiment, after receiving the detection data, the data processing unit 60 obtains the calibration position of the magnetic ball 10 according to the relationship between the three-axis magnetic field components and the rotation angle of the magnetic ball 10. Subsequently, the data processing unit 60 determines the angle by which the magnetic ball 10 needs to rotate according to the calibration position, and the driving unit drives the magnetic ball 10 to rotate, thereby completing the calibration. In one embodiment, the data processing unit 60 can be one or more processors.

For ease of installation and to improve measurement accuracy, in an optional embodiment, the first axis 110 or the second axis 120 passes through the three-axis magnetic field sensor 20. In this case, the position where the three-axis magnetic field sensor 20 is located can serve as the detection position.

As shown in FIG. 2, in a preferred embodiment of the present invention, the installation positions of the three-axis magnetic field sensor 20, the first driving unit 40, and the second driving unit 50 are relatively fixed, facilitating the integrated design of the magnetic ball calibration apparatus. To simplify the structure of a capsule endoscope system, in the embodiment of the present invention, the first driving unit 40 and the second driving unit 50 may be driving components on the magnetic control device within the capsule endoscope system that drive the rotation of the magnetic ball 10.

In an optional embodiment of the present invention, to support the three-axis magnetic field sensor 20, a magnetic field plate (not shown in FIGs) is arranged adjacent to the magnetic ball 10. The three-axis magnetic field sensor 20 is disposed on the magnetic field plate. The magnetic field plate is used to mount the three-axis magnetic field sensor 20, and its overall structure is flat, occupying little space, and it can comprehensively cover the magnetic ball 10. This facilitates flexible installation of the three-axis magnetic field sensor 20 and helps to reduce the overall size of the device. In other embodiments of the present invention, the magnetic field plate may also be another structure that fixes the three-axis magnetic field sensor 20, which is not elaborated further here.

In an optional embodiment of the present invention, the data processing unit 60 further comprises a third processing unit (not shown FIGs) and a fourth processing unit (not shown FIGs). The magnetic ball calibration apparatus further comprises a second driving unit 50. After the first driving unit 40 drives the magnetic ball 10 to rotate by a first angle around the first axis 110, it drives the magnetic ball 10 to rotate by a second angle around the first axis 110. After the magnetic ball 10 rotates by the second angle, the second driving unit 50 drives the magnetic ball 10 to rotate by a third angle around the second axis 120. The third processing unit is used to obtain the calibration position in the first direction based on the detection data of the three-axis magnetic field components and the corresponding rotation angle during the rotation of the magnetic ball 10 by the first angle around the first axis 110. The fourth processing unit is used to obtain the calibration position in the second direction based on the detection data of the three-axis magnetic field components obtained by the three-axis magnetic field sensor 20 and the corresponding rotation angle during the rotation of the magnetic ball 10 by the third angle around the second axis 120.

In an optional embodiment of the present invention, the magnetic ball calibration apparatus further comprises a readable storage medium for storing data. The readable storage medium is connected to the data processing unit 60 and the three-axis magnetic field sensor 20, respectively. Optionally, the readable storage medium is connected to the data processing unit 60 to store the data calculated by the data processing unit 60 and/or the data to be received by the data processing unit 60 (e.g., the detection data acquired by the three-axis magnetic field sensor 20 and/or the motion data of the magnetic ball 10). Optionally, the readable storage medium is connected to the three-axis magnetic field sensor 20 to store the detection data acquired by the three-axis magnetic field sensor 20.

Figure 4:
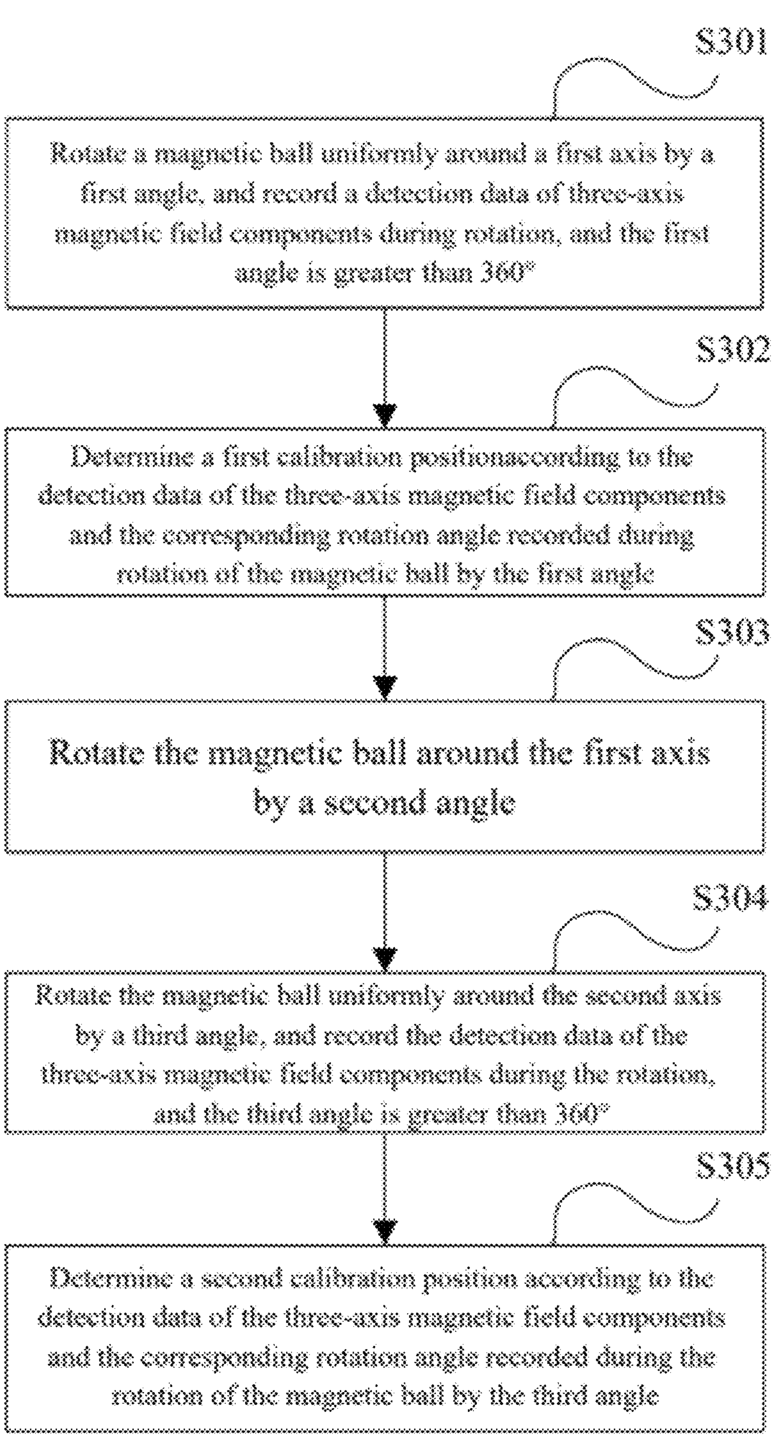
FIG. 4 shows a flowchart of the magnetic ball calibration method according to a second embodiment of the present invention.

FIG. 4 shows a flowchart of the magnetic ball calibration method according to a second embodiment of the present invention. According to the magnetic ball calibration method of the second embodiment of the present invention, the calibration position is the position where the magnetic field strength is the maximum value or the minimum value during the rotation of the magnetic ball 10. The method in this embodiment comprises the following steps:

step S301, rotating the magnetic ball 10 uniformly around the first axis 110 by a first angle, and recording the detection data of the three-axis magnetic field components during the rotation, where the first angle is greater than 360°.

In this step, during the rotation of the magnetic ball around the first axis 110, the three-axis magnetic field sensor 20 acquires the detection data $(b_{x0}, b_{y0}, b_{z0})$, $(b_{x1}, b_{y1}, b_{z1})$, . . . , $(b_{xn}, b_{yn}, b_{zn})$ of the three-axis magnetic field components at a plurality of sets of detection positions. The detection data of the three-axis magnetic field components has both positive value and negative value, with the positive and negative indicating the direction of the magnetic field.

Step S302, determining a first calibration position $V_0$ according to the detection data of the three-axis magnetic field components and the corresponding rotation angle recorded during the rotation of the magnetic ball 10 by the first angle.

According to the detection data of the three-axis magnetic field components during the rotation of the magnetic ball 10 by the first angle, the rotation angle of the magnetic ball 10 corresponding to the maximum magnetic field strength in the Z-axis direction during the measurement process is found, and a position corresponding to the found rotation angle is set as the first calibration position $V_0$.

Step 303, rotating the magnetic ball 10 around the first axis 110 by the second angle.

Optionally, the second angle is greater than or equal to 30° and smaller than or equal to 150°. Optionally, the second angle is greater than or equal to 10° and smaller than or equal to 80°. It should be noted that after the magnetic ball 10 is calibrated in the first direction, the magnetic field values measured by the three-axis magnetic field sensor 20 in the X-axis direction and Y-axis direction are very small and cannot be calibrated in the second direction. Therefore, the magnetic ball 10 is rotated by a certain angle (the second angle) around the first axis 110. In the above optional embodiment, the second angle is greater than or equal to 10° and smaller than or equal to 80° (the rotation angle is determined by the precision of the magnetic field sensor), where the higher the precision of the magnetic field sensor, the smaller the minimum rotation angle of the magnetic ball 10 can be.

In an optional embodiment of the present invention, the rotation of the magnetic ball 10 by the second angle is performed after the first calibration position $V_0$ is determined. After the magnetic ball 10 is rotated to the first calibration position $V_0$, the magnetic ball 10 is rotated by the second angle around the first axis 110 (i.e., the rotation of the second angle starts from the position of the magnetic ball 10 in the calibration position of the first direction).

Step S304, rotating the magnetic ball 10 uniformly around the second axis 120 by a third angle, and recording the detection data of the three-axis magnetic field components during the rotation, where the third angle is greater than 360°.

In this step, the magnetic ball 10 is rotated uniformly around the second axis 120 by a third angle, where the third angle is greater than 360°. The detection data $(b_{x0}, b_{y0}, b_{z0})$, $(b_{x1}, b_{y1}, b_{z1})$, . . . , $(b_{xn}, b_{yn}, b_{zn})$ of the three-axis magnetic field components at a plurality of sets of detection positions is recorded.

Step S305, determining a second calibration position $H_0$ according to the detection data of the three-axis magnetic field components and the corresponding rotation angle recorded during the rotation of the magnetic ball 10 by the third angle.

According to the detection data of the three-axis magnetic field components during the rotation of the magnetic ball 10 by the third angle, the rotation angle of the magnetic ball 10 corresponding to the maximum magnetic field strength in the Y-axis direction is found, and the position corresponding to the found rotation angle is set as the second calibration position $H_0$. Optionally, the position of the magnetic ball 10 corresponding to the maximum magnetic field strength in the X-axis direction is set as the second calibration position $H_0$.

In an optional embodiment of the present invention, after step S305, the method further comprises a step S306. Step S306, calibrating the magnetic ball 10 according to the first calibration position $V_0$ and the second calibration position $H_0$.

In this step, the magnetic ball 10 is calibrated according to the first calibration position $V_0$ and the second calibration position $H_0$. Where, the calibration of the magnetic ball 10 involves rotating the N magnetic pole and S magnetic pole of the magnetic ball 10 to the second axis 120 or the first axis 110.

Figure 5:
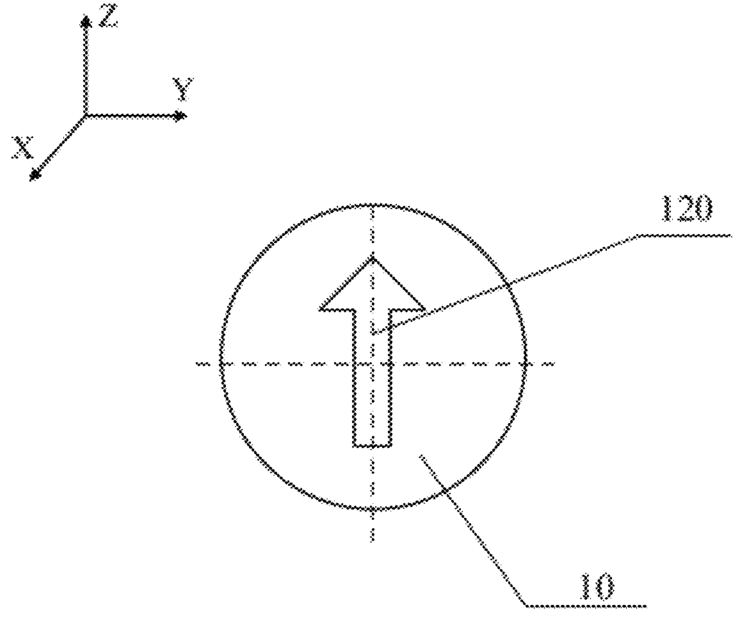
FIG. 5 shows a schematic diagram after calibration of the magnetic ball according to an embodiment of the present invention.

FIG. 5 shows a schematic diagram after calibration of the magnetic ball according to an embodiment of the present invention. As shown in FIG. 5, after the calibration of the magnetic ball 10 according to an embodiment of the present invention, the main axis of the magnetic ball (i.e., the straight line on which the N magnetic pole and S magnetic pole are located) coincides with the second axis 120.

Figure 6:
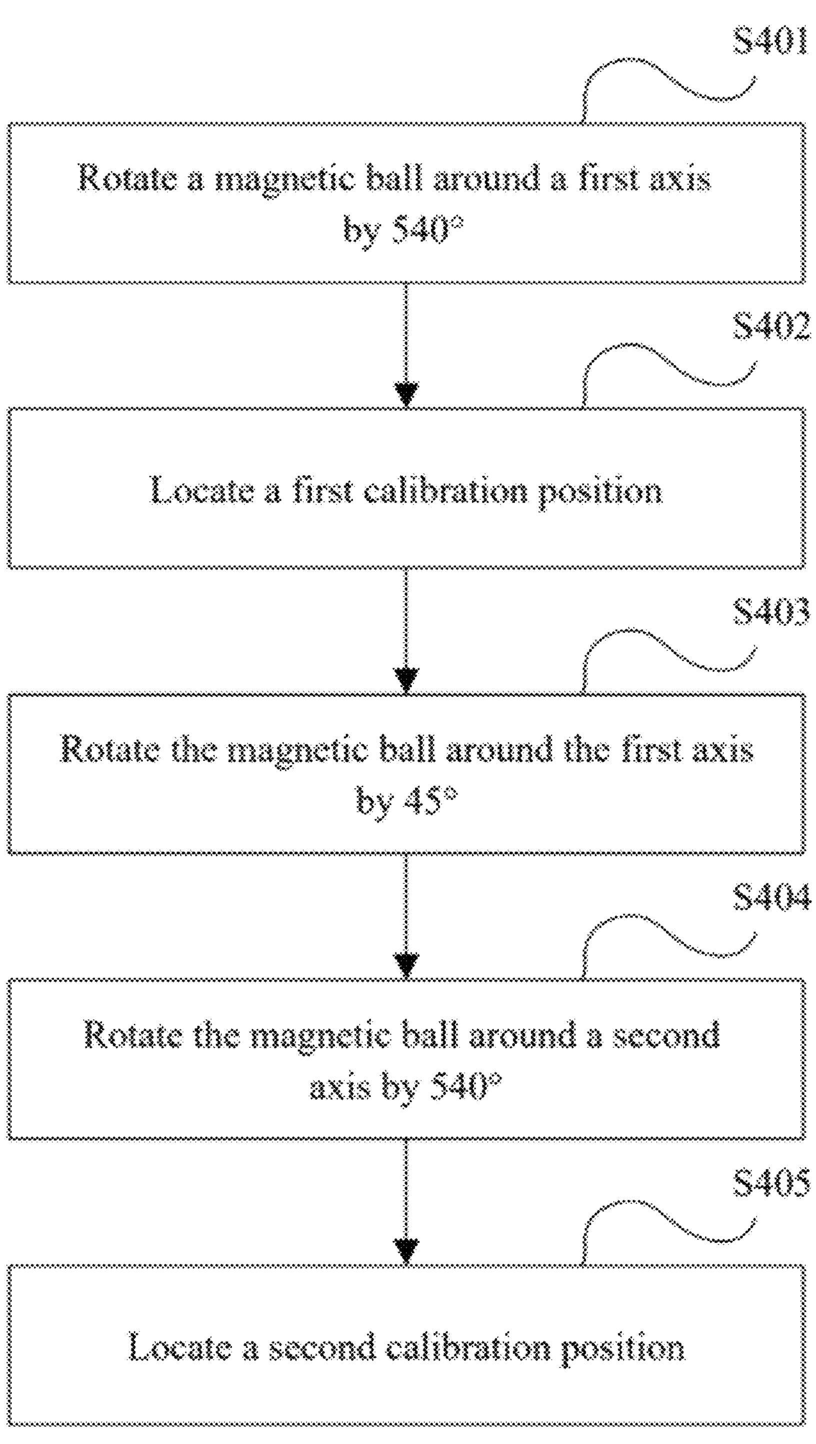
FIG. 6 shows a flowchart of the magnetic ball calibration method according to an optional embodiment of the second embodiment of the present invention.

FIG. 6 shows a flowchart of the magnetic ball calibration method according to an optional embodiment of the second embodiment of the present invention. To balance the completeness of detection data and the simplicity of control, this optional embodiment determines an appropriate rotation angle for the magnetic ball. The magnetic ball calibration method in this embodiment specifically comprises the following steps:

Step S401, rotating the magnetic ball 10 around the first axis (in the first direction) by 540°.

Step S402, locating the first calibration position $V_0$.

Recording the change in magnetic field strength at the detection position (e.g., directly above the magnetic ball 10) during the rotation of the magnetic ball 10 around the first axis 110, and setting the position of the magnetic ball 10 corresponding to the maximum magnetic field strength in the Z-axis direction at the detection position (e.g., directly above the magnetic ball 10) as the first calibration position $V_0$.

Step 403, rotating the magnetic ball 10 around the first axis 110 by 45°.

Step S404, rotating the magnetic ball 10 around the second axis (in the second direction) by 540°.

Step S405, locating the second calibration position $H_0$.

Recording the change in magnetic field strength at the detection position during the rotation of the magnetic ball 10 around the first axis 110, and setting the position of the magnetic ball 10 corresponding to the maximum magnetic field strength in the Y-axis direction at the detection position (e.g., directly above the magnetic ball 10) as the second calibration position $H_0$. Alternatively, setting the position of the magnetic ball 10 corresponding to the maximum magnetic field strength in the X-axis direction (perpendicular to both the first axis 110 and the second axis 120) at the detection position as the second calibration position $H_0$.

Figure 7:
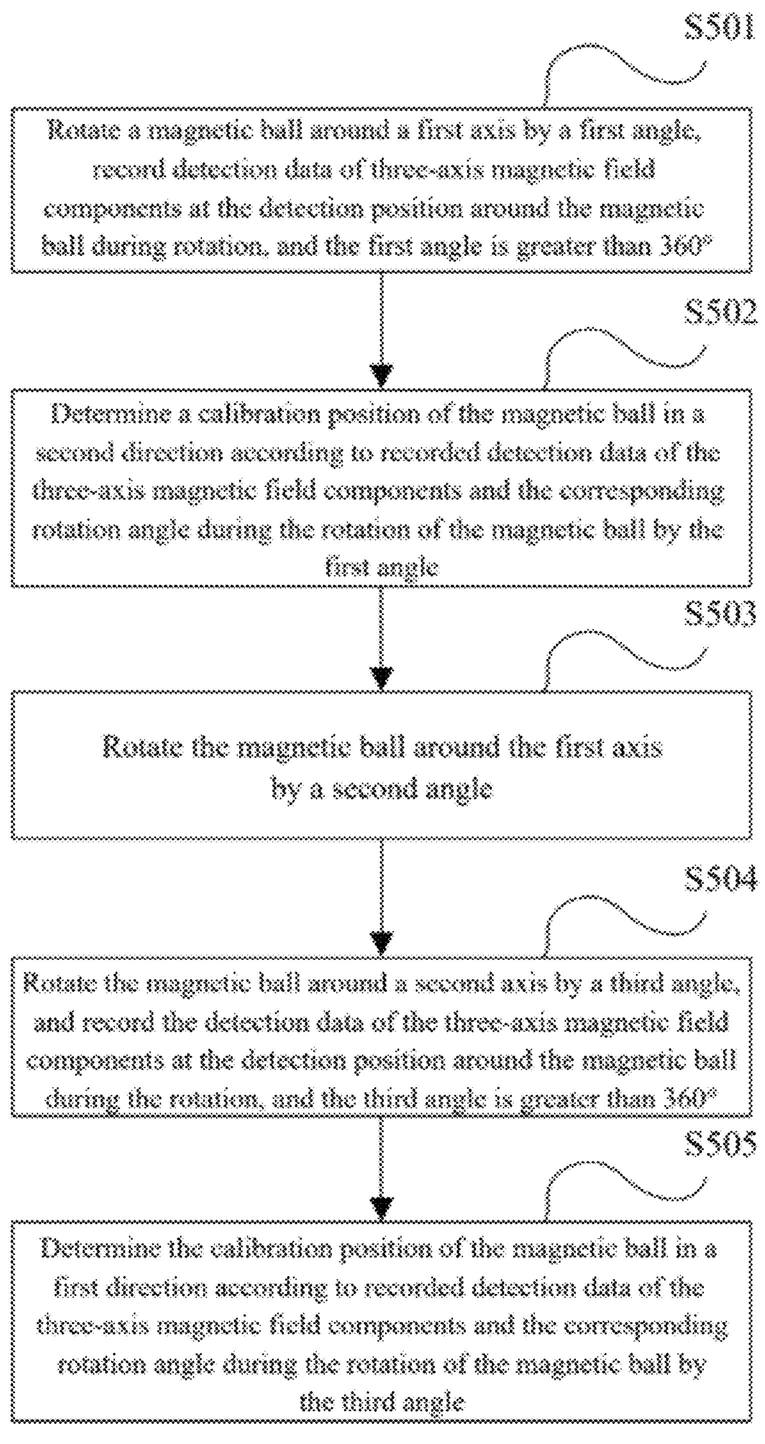
FIG. 7 shows a flowchart of the magnetic ball calibration method according to a third embodiment of the present invention.

FIG. 7 shows a flowchart of the magnetic ball calibration method according to a third embodiment of the present invention. To further improve data accuracy and thereby the calibration accuracy of the magnetic ball 10, the magnetic ball calibration method according to the third embodiment of the present invention is an improvement on the magnetic ball calibration method of the previous embodiments. For convenience of description, the directions of the X-axis, Y-axis, and Z-axis of the three-axis magnetic field sensor 20 in this embodiment are consistent with those in the previous embodiments. The specific steps of the method in this embodiment comprise:

- step S501, rotating the magnetic ball 10 around the first axis 110 by a first angle, recording the detection data of the three-axis magnetic field components at the detection position around the magnetic ball 10 during the rotation, where the first angle is greater than 360°.

In this step, the three-axis magnetic field sensor 20 can record the reading of the detection data of the three-axis magnetic field components at different angles of rotation of the magnetic ball 10. Optionally, according to the detection data of the three-axis magnetic field components in the Z-axis direction at the detection position, processing the angle of rotation of the magnetic ball 10 as the independent variable and the magnetic field value as the dependent variable to obtain the magnetic field value variation curve in a selected direction (Z-axis direction) at the detection position. The magnetic field values have both positive value and negative value, indicating the direction of the magnetic field.

In an optional embodiment of the present invention, the data processing unit of the magnetic ball calibration apparatus further comprises a fifth processing unit. The fifth processing unit uses the angle of rotation of the magnetic ball 10 as the independent variable and the measured magnetic field value at the detection position as the dependent variable to obtain the variation of the magnetic field value in the Z-axis direction at the detection position with the angle of rotation of the magnetic ball 10, and plots the magnetic field value variation curve in the Z-axis direction at the detection position.

Step S502, determining the calibration position of the magnetic ball 10 in the second direction according to the recorded detection data of the three-axis magnetic field components and the corresponding rotation angle during the rotation of the magnetic ball 10 by the first angle.

Finding the extreme values (maximum value and minimum value) in the Z-axis direction among the detection data of the three-axis magnetic field components during the rotation of the magnetic ball 10 by the first angle, and determining the calibration position of the magnetic ball 10 in the second direction according to the extreme values and the corresponding rotation angles. Specifically, the positions of the magnetic ball 10 corresponding to the extreme values in the Z-axis direction among the detection data of the three-axis magnetic field components can all be used as the calibration position of the magnetic ball 10 in the second direction, and the unique first calibration position $V_0$ can be determined based on actual needs.

It should be noted that if the recorded detection data of the three-axis magnetic field components in the Z-axis direction are all zero during the rotation of the magnetic ball 10 by the first angle, it indicates that the N magnetic pole and S magnetic pole of the magnetic ball 10 are both located on the first axis 110 (i.e., the magnetic polarization direction of the magnetic ball 10 coincides with the first axis 110). In this case, the N magnetic pole and/or the S magnetic pole can be used as calibration references to calibrate the magnetic ball 10.

Step 503, rotating the magnetic ball 10 around the first axis 110 by the second angle.

Where the second angle is greater than or equal to 30° and smaller than or equal to 150°.

Step S504, rotating the magnetic ball 10 around the second axis 120 by a third angle, and recording the detection data of the three-axis magnetic field components at the detection position around the magnetic ball 10 during the rotation, where the third angle is greater than 360°.

In this step, the magnetic ball 10 is rotated around the second axis 120 by a third angle, where the third angle is greater than 360°. The readings of the detection data of the three-axis magnetic field components at different angles of rotation of the magnetic ball 10 are recorded. Optionally, recording the magnetic field data at the detection position, treating the angle of rotation of the magnetic ball 10 as the independent variable and the magnetic field value as the dependent variable to obtain the magnetic field value variation curve in the Y-axis direction or the X-axis direction at the detection position. The magnetic field values have both positive value and negative value, indicating the direction of the magnetic field.

Optionally, in one embodiment, the acquired magnetic field values and corresponding angles are reflected as discrete points on the graph. By a method such as a direct line or an interpolation method, a curve is drawn by connecting each discrete point, and through the curve, the magnetic field value corresponding to any angle can be obtained.

In another embodiment, the acquired magnetic field values and corresponding angles are reflected as discrete points on the graph and are fitted to a sine curve. The sine curve thus obtained can be used to obtain the magnetic field value corresponding to any angle.

In other embodiments, based on the measured magnetic field values, other methods can also be used to obtain the curve representing the relationship between the magnetic field value and the angle of rotation of the magnetic ball 10, and the calibration position of the magnetic ball 10 can be determined from the curve. In some another embodiments, if the rotation of the magnetic ball 10 and the time are consistent, the calibration position of the magnetic ball 10 can also be determined by the curve of the magnetic field value and the time of the rotation of the magnetic ball 10.

Step S505, determining the calibration position of the magnetic ball 10 in the first direction according to the recorded detection data of the three-axis magnetic field components and the corresponding rotation angle during the rotation of the magnetic ball 10 by the third angle.

Finding the extreme values (maximum value and minimum value) in the Y-axis direction among the detection data of the three-axis magnetic field components during the rotation of the magnetic ball 10 by the third angle, and determining the calibration position of the magnetic ball 10 in the Y-axis direction according to the rotation angles corresponding to the extreme values. Alternatively, finding the extreme values in the X-axis direction among the detection data of the three-axis magnetic field components during the rotation of the magnetic ball 10 by the third angle, and determining the calibration position of the magnetic ball 10 in the X-axis direction according to the extreme values and the corresponding rotation angles. Specifically, the rotation angles of the magnetic ball 10 corresponding to the extreme values in the Y-axis direction or the X-axis direction among the detection data of the three-axis magnetic field components can all be used as the calibration position of the magnetic ball 10 in the Y-axis direction or the X-axis direction, and the unique second calibration position $H_0$ can be determined based on actual needs.

In an optional embodiment of the present invention, after step S505, the method further comprises a step S506. Step S506, calibrating the magnetic ball 10 according to the calibration position in the first direction and the calibration position in the second direction.

Calibrating the magnetic ball 10 according to the second calibration position $H_0$ in the second direction and the first calibration position $V_0$ in the first direction. Optionally, calibrating the magnetic ball 10, i.e. rotating the N magnetic pole and S magnetic pole of the magnetic ball 10 to the second axis 120 or the first axis 110.

In an optional embodiment of the present invention, between steps S502 and S503, the method further comprises the following step:

rotating the magnetic ball 10 to the second calibration position $H_0$ in the second direction.

In an optional embodiment of the present invention, during the rotation of the magnetic ball 10 by the first angle and/or the second angle and/or the third angle, the rotation is at a constant speed.

In the above embodiments of the present invention, by treating the angle of rotation of the magnetic ball 10 as the independent variable and the acquired detection data (magnetic field values) of the three-axis magnetic field components as the dependent variable to plot a curve, the acquired measurements are plotted into a curve, which can provide the magnetic field value corresponding to any angle, thereby improving data accuracy and further enhancing the calibration (adjustment) accuracy of the magnetic ball 10.

Figure 8:
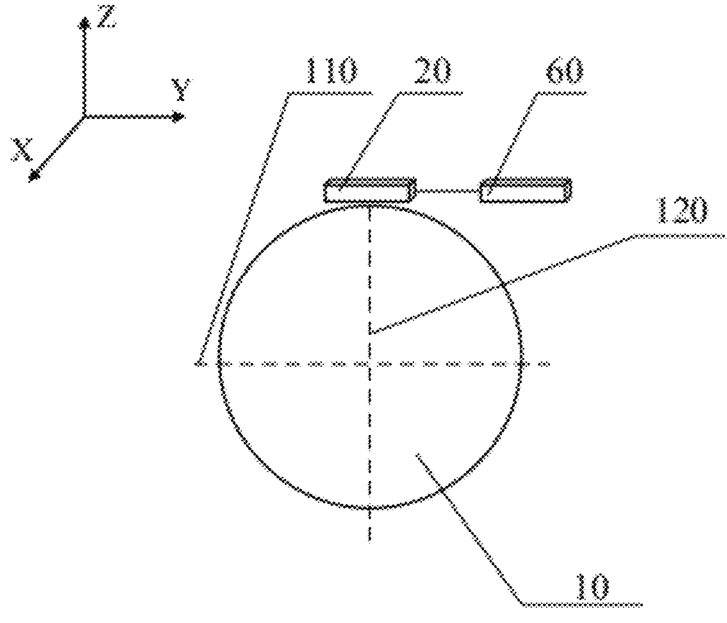
FIG. 8 shows a structural diagram of the magnetic ball calibration apparatus according to a fourth embodiment of the present invention.

FIG. 8 shows a structural diagram of the magnetic ball calibration apparatus according to a fourth embodiment of the present invention. As shown in FIG. 8, the magnetic ball calibration apparatus according to a fourth embodiment of the present invention comprises a three-axis magnetic field sensor 20 and a data processing unit 60. The magnetic ball 10 rotates around the first axis 110 and/or the second axis 120.

The magnetic ball 10 is in the three-dimensional Cartesian coordinate system as shown in FIG. 8, and can rotate around the first axis 110 (Y-axis) and the second axis 120 (Z-axis) to achieve rotation of the magnetic ball 10 in any direction.

The three-axis magnetic field sensor 20 is located directly above the magnetic ball 10 (above the magnetic ball 10 in the Z-axis direction) to detect the magnetic field strength of the magnetic ball 10 in three-dimensional space.

The data processing unit 60 is connected to the three-axis magnetic field sensor 20 to receive the detected magnetic field strength and process the data.

Figure 9:
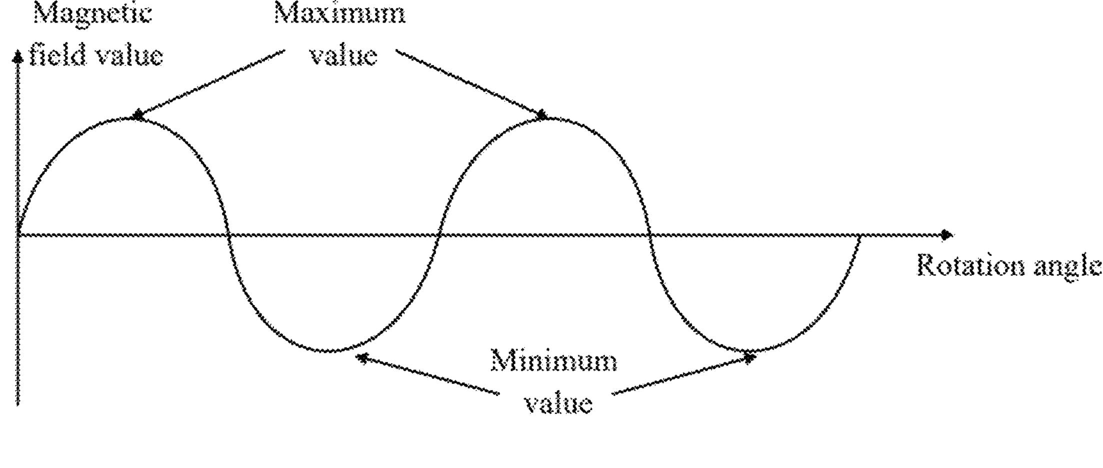
FIG. 9 shows a periodic change curve of magnetic field values according to an embodiment of the present invention.

FIG. 9 shows a periodic variation curve of magnetic field values according to an embodiment of the present invention. As shown in FIG. 9, the horizontal axis represents the rotation angle of the magnetic ball, and the vertical axis represents the detected magnetic field value (e.g., the data in any direction of the three-axis magnetic field components). The detected magnetic field value changes periodically with the rotation angle of the magnetic ball. According to the calibration method of the present invention, during the rotation of the magnetic ball 10 (around the first axis or the second axis), the magnetic field value (in the Z-axis direction or Y-axis direction) and the corresponding angles are recorded to plot the periodic variation curve of the magnetic field value, as shown in FIG. 9. The curve has two types of vertices, one for the maximum value and one for the minimum value. The magnetic ball 10 rotates by 180° between these two adjacent extreme values. The positions corresponding to the maximum value and minimum value of the magnetic field value can be used as the calibration positions of the magnetic ball 10 (in the first direction or the second direction), and the specific calibration position can be determined based on actual needs.

It should be noted that, relationship terms as described herein such as first and second are used only to distinguish one entity or operation from another, but do not necessarily require or imply any such actual relationship or sequence between these entities or operations. Moreover, the terms "include", "comprise" or any other variant thereof are intended to cover non-exclusive inclusion, so that a process, method, article or device that includes a series of elements includes not only those elements but also other elements that are not explicitly listed or further includes the elements inherent to such process, method, article or device. Without further limitation, the element limited by the statement "includes a . . . " does not preclude the existence of another identical element in the process, method, article or equipment that includes aforementioned element.

In accordance with embodiments of the present invention as described above, the embodiments do not elaborate all details, and do not limit the invention to the embodiments. Obviously, a plurality of modifications and changes can be made based on the above description. These embodiments have been selected and specifically described in this specification in order to better explain the principles and practical applications of the present invention, so those skilled in the art can make good use of the present invention and the modify based on the present invention. The present invention is limited only by the claims and their full scope and equivalents.

The invention claimed is:

1. A magnetic ball calibration method, comprising:

rotating a magnetic ball around a first axis and a second axis, and acquiring detection data of three-axis magnetic field components at a detection position during rotation;

obtaining a calibration position of the magnetic ball according to the detection data; and calibrating the magnetic ball according to the calibration position of the magnetic ball;

wherein when the magnetic ball is located at the calibration position, the magnetic polarization direction of the magnetic ball coincides with the second axis;

the first axis is perpendicular to the second axis;

the three-axis magnetic field components comprise an X-axis magnetic field component, a Y-axis magnetic field component and a Z-axis magnetic field component;

the direction of the Z-axis magnetic field component coincides with the direction of the second axis, and the direction of the Y-axis magnetic field component coincides with the direction of the first axis.

2. The magnetic ball calibration method of claim 1, wherein rotating the magnetic ball around the first axis by a first angle, and acquiring detection data of the three-axis magnetic field components at a detection position during the rotation;

obtaining a first calibration position $V_0$ of the magnetic ball rotating around the first axis according to the detection data of the three-axis magnetic field components and the corresponding rotation angle during the rotation of the magnetic ball around the first axis by the first angle;

rotating the magnetic ball to the first calibration position $V_0$, and then rotating the magnetic ball around the first axis by a second angle;

rotating the magnetic ball around the second axis by a third angle, and acquiring detection data of the three-axis magnetic field components at a detection position during the rotation;

obtaining a second calibration position Ho of the magnetic ball rotating around the second axis according to the detection data of the three-axis magnetic field components and the corresponding rotation angle during the rotation of the magnetic ball by the third angle.

3. The magnetic ball calibration method of claim 2, wherein the first angle is greater than 360°, or is 540°;

the second angle is greater than or equal to 10° and smaller than or equal to 80°, or is 45°; and the third angle is greater than 360°, or is 540°.

4. The magnetic ball calibration method of claim 2, wherein obtaining the first calibration position $V_0$ of the magnetic ball rotating around the first axis comprises:

determining the position of the magnetic ball corresponding to the maximum value or minimum value of the magnetic field strength in the Z-axis direction as the first calibration position $V_0$ according to the detection data of the three-axis magnetic field components and the corresponding rotation angle during the rotation of the magnetic ball around the first axis by the first angle;

obtaining the second calibration position Ho of the magnetic ball rotating around the second axis comprises:

determining the rotation angle corresponding to the maximum value or minimum value of the magnetic field strength in the Y-axis direction as the second calibration position Ho according to the detection data of the three-axis magnetic field components and the corresponding rotation angle during the rotation of the magnetic ball around the second axis by the third angle;

or, determining the rotation angle corresponding to the maximum value or minimum value of a magnetic field strength in the X-axis direction as the second calibration position $H_0$ according to the detection data of the three-axis magnetic field components and the corresponding rotation angle during the rotation of the magnetic ball around the second axis by the third angle.

5. The magnetic ball calibration method of claim 2 er 3, wherein obtaining the first calibration position $V_0$ of the magnetic ball rotating around the first axis comprises:

obtaining a curve of a magnetic field strength in the Z-axis direction with respect to the rotation angle of the magnetic ball according to the detection data during the rotation of the magnetic ball around the first axis by the first angle, wherein the rotation angle of the magnetic ball corresponding to the maximum value or minimum value on the curve is the first calibration position $V_0$; and obtaining the second calibration position Ho of the magnetic ball rotating around the second axis comprises:

obtaining a curve of the magnetic field strength in the Y-axis direction with respect to the rotation angle of the magnetic ball according to the detection data during the rotation of the magnetic ball around the second axis by the third angle, and determining the rotation angle corresponding to the maximum value or minimum value of the magnetic field strength in the Y-axis direction as the second calibration position $H_0$;

or, determining the rotation angle corresponding to the maximum value or minimum value of the magnetic field strength in the X-axis direction as the second calibration position $H_0$ according to the detection data of the three-axis magnetic field components and the corresponding rotation angle during the rotation of the magnetic ball around the second axis by the third angle.

6. A magnetic ball calibration apparatus, wherein the magnetic ball comprises magnetic poles along a main axis direction, comprising:

a driving unit for driving the magnetic ball to rotate, comprising a first driving unit and a second driving unit, wherein the first driving unit is used to drive the magnetic ball to rotate around a first axis, and the second driving unit is used to drive the magnetic ball to rotate around a second axis, and calibrate the magnetic ball based on the calibration position;

a three-axis magnetic field sensor, disposed adjacent to the magnetic ball to obtain detection data of three-axis magnetic field components during rotation of the magnetic ball; and a data processing unit, connected to the three-axis magnetic field sensor to receive the detection data of the three-axis magnetic field components, and obtain the calibration position of the magnetic ball according to the detection data changing with the rotation angle during rotation of the magnetic ball, wherein, when the magnetic ball is at the calibration position, the main axis coincides with the second axis;

the first axis is perpendicular to the second axis;

the three-axis magnetic field components comprise an X-axis magnetic field component, a Y-axis magnetic field component and a Z-axis magnetic field component;

the direction of the Z-axis magnetic field component coincides with the direction of the second axis, and the direction of the Y-axis magnetic field component coincides with the direction of the first axis.

7. The magnetic ball calibration apparatus of claim 6, wherein the first driving unit is used to drive the magnetic ball to rotate around the first axis by a first angle;

the data processing unit comprises a third processing unit, the third processing unit used for obtaining a first calibration position $V_0$ of the magnetic ball rotating around the first axis according to the detection data of the three-axis magnetic field components and the corresponding rotation angle during the rotation of the magnetic ball by the first angle around the first axis;

the first driving unit rotates the magnetic ball to the first calibration position $V_0$, and the first driving unit is also used to rotate the magnetic ball around the first axis by a second angle;

the second driving unit is used to drive the magnetic ball to rotate around the second axis by a third angle;

the data processing unit comprises a fourth processing unit, the fourth processing unit used for obtaining a second calibration position Ho of the magnetic ball rotating around the second axis according to the detection data of the three-axis magnetic field components and the corresponding rotation angle during the rotation of the magnetic ball by the third angle around the second axis.

8. The magnetic ball calibration apparatus of claim 7, wherein the first angle is greater than 360°, or is 540°;

the second angle is greater than or equal to 10° and smaller than or equal to 80°, or is 45°; and the third angle is greater than 360°, or is 540°.

9. The magnetic ball calibration apparatus of claim 7, wherein the third processing unit is also used for:

determining the position of the magnetic ball corresponding to the maximum value or minimum value of a magnetic field strength in the Z-axis direction as the first calibration position $V_0$ according to the detection data of the three-axis magnetic field components and the corresponding rotation angle during the rotation of the magnetic ball around the first axis by the first angle;

the fourth processing unit is also used for:

determining the rotation angle corresponding to the maximum value or minimum value of the magnetic field strength in the Y-axis direction as the second calibration position $H_0$ according to the detection data of the three-axis magnetic field components and the corresponding rotation angle during the rotation of the magnetic ball around the second axis by the third angle;

or, determining the rotation angle corresponding to the maximum value or minimum value of the magnetic field strength in the X-axis direction as the second calibration position $H_0$ according to the detection data of the three-axis magnetic field components and the corresponding rotation angle during the rotation of the magnetic ball around the second axis by the third angle.

10. The magnetic ball calibration apparatus of claim 7, wherein the third processing unit is also used for:

obtaining a curve of the three-axis magnetic field component in the Z-axis direction with respect to the rotation angle of the magnetic ball according to the detection data during the rotation of the magnetic ball around the first axis by the first angle, wherein the rotation angle of the magnetic ball corresponding to the maximum value or minimum value on the curve is the first calibration position $V_0$;

the fourth processing unit is also used for:

obtaining a curve of the three-axis magnetic field component in the Y-axis direction with respect to the rotation angle of the magnetic ball according to the detection data during the rotation of the magnetic ball around the second axis by the third angle, and determining the rotation angle corresponding to the maximum value or minimum value of a magnetic field strength in the Y-axis direction as the second calibration position $H_0$;

or, determining the rotation angle corresponding to the maximum value or minimum value of the magnetic field strength in the X-axis direction as the second calibration position $H_0$ according to the detection data of the three-axis magnetic field components and the corresponding rotation angle during the rotation of the magnetic ball by the third angle.

11. The magnetic ball calibration apparatus of claim 6, wherein the first axis or the second axis passes through the three-axis magnetic field sensor; and the detection position comprises the position where the three-axis magnetic field sensor is located.

* * * * *